United States Patent
Luther et al.

(12)

(10) Patent No.: US 6,201,000 B1
(45) Date of Patent: *Mar. 13, 2001

(54) USE OF SELECTED BENZOTRIAZOLE DERIVATIVES FOR PROTECTING HUMAN AND ANIMAL SKIN AND HAIR FROM THE HARMFUL EFFECTS OF UV RADIATION

(75) Inventors: Helmut Luther, Grenzach-Wyhlen; Dieter Reinehr, Kandern, both of (DE); Rudolf Zink, Therwil (CH)

(73) Assignee: Ciba Specialty Chemicals Corporation, Tarrytown, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/308,423

(22) PCT Filed: Nov. 13, 1997

(86) PCT No.: PCT/EP97/06330

§ 371 Date: May 18, 1999

§ 102(e) Date: May 18, 1999

(87) PCT Pub. No.: WO98/23252

PCT Pub. Date: Jun. 4, 1998

(30) Foreign Application Priority Data

Nov. 22, 1996 (CH) .................................................. 2885/96

(51) Int. Cl.$^7$ ...................................................... A61K 31/41
(52) U.S. Cl. ............................................................ 514/383
(58) Field of Search ...................................... 430/512, 507, 430/514; 524/91; 351/160 H; 548/260; 514/383

(56) References Cited

U.S. PATENT DOCUMENTS

| 4,528,311 | * | 7/1985 | Beard et al. | ........................... 524/91 |
| 5,500,332 | | 3/1996 | Vishwakarma et al. . | |
| 5,569,451 | * | 10/1996 | Richard et al. | ......................... 424/59 |
| 5,629,365 | * | 5/1997 | Razavi | .................... 524/37 |
| 5,766,834 | * | 6/1998 | Chen et al. | .......................... 430/512 |

FOREIGN PATENT DOCUMENTS

| 2194442 | 3/1974 | (FR) . |
| 2288613 | 10/1995 | (GB) . |

* cited by examiner

Primary Examiner—William R. A. Jarvis
Assistant Examiner—Vickie Kim
(74) Attorney, Agent, or Firm—Kevin T. Mansfield

(57) ABSTRACT

The invention is related to a composition containing benzotriazole derivatives of formula (I) and the method of treating skin damages due to harmful UV radiation using this claimed composition.

12 Claims, No Drawings

USE OF SELECTED BENZOTRIAZOLE DERIVATIVES FOR PROTECTING HUMAN AND ANIMAL SKIN AND HAIR FROM THE HARMFUL EFFECTS OF UV RADIATION

This application is a 371 of PCT EP97/06330 field Nov. 11, 1997.

The present invention relates to the use of selected benzotriazole derivatives for protecting human and animal hair and skin from the harmful effects of UV radiation.

It is known that UV radiation having a wavelength of 285 to 400 nm causes or accelerates a very wide range of skin damages in humans, for example erythemas, accelerated skin ageing, phototoxic and photoallergic reactions and the like. If human hair is exposed to sunlight over a prolonged period of time it may be damaged in different ways. Under the influence of sunlight, dyed hair can change its colour and shade. Blond hair turns yellowish. The hair surface becomes rougher and at the same time drier. Furthermore, the hair gradually loses its sheen.

Chemical compounds in the form of cosmetic formulations recommending themselves for the topical protection of human skin and of the hair surface are therefore those which are able to reduce or prevent the mentioned harmful effects of UV radiation.

Surprisingly, it has now been found that specific benzotriazole derivatives have excellent substantivity for human hair while at the same time providing effective UV protection for hair and human skin.

Accordingly, this invention relates to the use of selected benzotriazole derivatives for protecting human and animal hair and skin from the harmful effects of UV radiation.

The selected benzotriazole compounds are compounds of formula

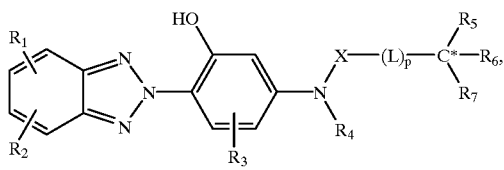

(1)

wherein $R_1$, $R_2$ and $R_3$ are each independently of one another hydrogen; straight-chain or branched $C_1$–$C_{22}$alkyl; hydroxy; carboxy; carbo-$C_1$–$C_{22}$alkoxy; nitro; $C_2$–$C_{22}$alkylcarbonylamino; $C_5$–$C_8$-Cacycloalkyl; carbamoyl; sulfonyl; sulfamoyl; sulfonamido; $C_2$–$C_{22}$alkylcarbonyloxy; cyano; halogen; $C_6$–$C_{12}$aryl or $C_4$–$C_{12}$heteroaryl which is unsubstituted or substituted by one or several $C_1$–$C_4$alkyl; $C_7$–$C_{10}$aralkyl which is unsubstituted or substituted by one or several $C_1$–$C_4$alkyl; $C_8$–$C_{12}$aryloxy; or a radical of formula

(1a)

wherein $A_1$ is straight-chain or branched $C_1$–$C_8$alkyl; $C_5$–$C_8$cycloalkyl; $C_5$–$C_{12}$aryl which is unsubstituted or substituted by one or several $C_1$–$C_4$alkyl; or $C_7$–$C_{10}$aralkyl which is unsubstituted or substituted by one or several $C_1$–$C_4$alkyl;

$m_1$ is 1 to 10;

Q is —O—; —S—; or —NH—; or $R_1$ and $R_2$, together with the benzene ring of the benzotriazole, are a $C_5$–$C_{18}$aryl ring or a $C_4$–$C_{16}$heteroaryl ring, which rings are unsubstituted or substituted by $C_1$–$C_{22}$alkyl or $C_1$–$C_{22}$alkoxy;

$R_4$ is hydrogen; $C_1$–$C_{22}$alkyl which is unsubstituted or substituted by 1 to 5 halogen atoms and/or which is interrupted by a —C(O)—O— or —SO$_2$—O— group;

$R_5$, $R_6$, $R_7$ are each independently of one another hydrogen; halogen; cyano; straight-chain or branched $C_1$–$C_{22}$alkyl; straight-chain or branched $C_1$–$C_{22}$alkoxy; $C_5$–$C_{12}$aryl; straight-chain or branched $C_1$–$C_{22}$thioalkyl; mono- or di-$C_1$–$C_{22}$alkylamino; mono- or di-$C_6$–$C_{12}$-arylamino; $R_5 \neq R_6 \neq R_7$;

X is

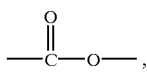

the carbonyl carbon atom being bound to the nitrogen atom of the

moiety; or —SO$_2$—;

L is a divalent radical consisting of 1 to 20 atoms; and p is 0 or 1.

Straight-chain and branched $C_1$–$C_{22}$alkyl is typically methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl. isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, heptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl or eicosyl.

$C_5$–$C_8$Cycloalkyl is typically cyclopentyl, cycloheptyl, cyclooctyl and, in particular, cyclohexyl.

Examples of $C_6$–$C_{12}$aryl to be mentioned are, in particular, phenyl, naphthyl and biphenyl.

Typical examples of $C_7$–$C_{10}$aralkyl are benzyl, phenethyl, α-methylphenethyl or α,α-dimethylbenzyl.

"Alkylene" in formula (1a) is a divalent alkylene group containing 2 to 5, preferably 2 to 4 carbon atoms. It is preferably the —CH$_2$—CH$_2$—; —CH$_2$CH$_2$CH$_2$—;

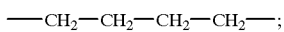

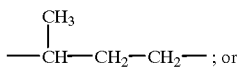

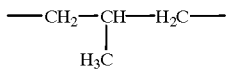

group. Of these alkylene groups, the —$CH_2$—$CH_2$— and the

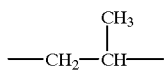

group are very particularly preferred.

Halogen is fluoro, bromo or, preferably, chloro.

The compound of formula (1) is preferably a 60:40 to 40:60 mixture of two enantiomers relative to the asymmetrical C* atom.

L can consist, in particular, of 1 to 20 atoms and can be a straight-chain or branched alkylene group which may be interrupted by 1 to 5 oxygen, sulfur or nitrogen atoms or by a —C(O)—O— group which is unsubstituted or substituted by $C_1$–$C_{10}$alkoxy, $C_1$–$C_{10}$alkylcarbonyloxy, $C_1$–$C_{10}$alkyl sulfide, amino, mono-$C_1$–$C_{10}$alkylamino, di-$C_1$–$C_{10}$alkylmino or halogen; or the divalent radical of a 4- to 6-membered alicyclic ring or of a heterocyclic ring containing 1 to 3 hetero atoms.

Illustrative examples of alicyclic and heterocyclic radicals are heterocyclic radicals containing cyclohexylene, pyrrolidinylene, tetrahydofuranylene, tetrahydrothienylene, piperidinylene, pyrrolylene, furylene, thienylene, pyrridylene or Spiro ethers, for example

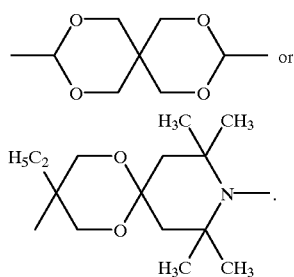

In particular, L may also be a methine group which is unsubstituted or substituted by $C_1$–$C_{12}$-alkyl or $C_1$–$C_{12}$alkoxy, amino, mono- or di-$C_1$–$C_6$alkylamino or halogen, wherein $C_1$–$C_{12}$alkyl or $C_1$–$C_{12}$alkoxy may be interrupted by 1 or 2 oxygen atoms.

Typical examples of L defined as divalent radicals are:

alkylene groups, such as —$CH_2$—; $CH_2$—$CH_2$—; —$CH_2CH_2CH_2$—;

—$CH_2$—$CH_2$—$CH_2$—$CH_2$—;

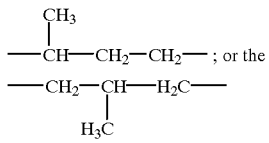

group. Of these alkylene groups, the —$CH_2$— and the —$CH_2$—$CH_2$— group are very particularly preferred.

Radicals containing oxygen atoms or —C(O)—O— groups, such as —$CH_2$—O—$CH_2$—$CH_2$—O—; —($CH_2$—O—$CH_2$—$CH_2$—O)$_2$—; —$CH_2$—C(O)O$CH_2$—; —$CH_2$C(O)OCH$_2$CH(OCOCH$_3$)CH$_2$O—;

heterocyclic radicals, such as

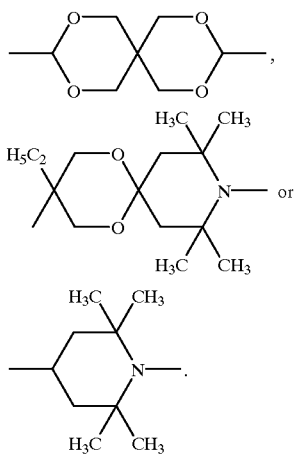

$R_5$, $R_6$, $R_7$ in formula (1) are preferably each hydrogen; or, independently of one another, straight-chain or branched $C_1$–$C_{22}$alkyl.

According to this invention, it is very particularly preferred to use benzotriazole derivatives of formula (2)

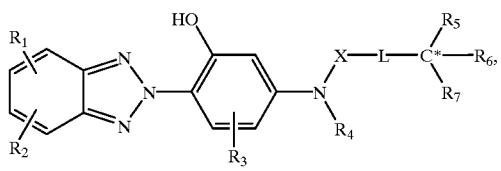

wherein $R_1$ and $R_2$ are each independently of one another hydrogen; halogen; $C_1$–$C_5$alkyl; $C_1$–$C_5$-alkoxy; mono- or di-$C_1$–$C_5$alkylamino; or $C_1$–$C_5$alkyl sulfide;

$R_3$ is hydrogen; hydroxy; or halogen;

$R_4$ is hydrogen; $C_1$–$C_5$alkyl which is unsubstituted or substituted by 1 to 5 halogen atoms and/or which may be interrupted by a —C(O)—O— or —$SO_2$—O— group;

L is a straight-chain or branched alkylene group which may be interrupted by 1 to 5 oxygen atoms or by a —C(O)—O— group which may be substituted by $C_1$–$C_{10}$alkoxy or $C_1$–$C_{10}$-alkylcarbonyloxy; and $R_5$, $R_6$, $R_7$ are each independently of one another hydrogen or $C_1$–$C_{10}$alkyl; $R_5 \neq R_6 \neq R_7$; and X is

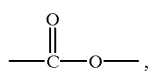

the carbonyl carbon atom being bound to the nitrogen atom of the

moiety; or —$SO_2$—.

Very particularly preferred benzotriazole derivatives are those of formula (3)

[Chemical structure showing benzotriazole derivative with R1, R2, R3, R4, R5, R6, R7, X, L substituents and HO, H groups]

wherein $R_3$ is hydrogen; halogen or hydroxy;

$R_4$ is hydrogen; $C_1$–$C_5$alkyl which is unsubstituted or substituted by 1 to 5 halogen atoms and/or which may be interrupted by a —C(O)—O— or —SO$_2$—O— group;

$R_5$, $R_6$, $R_7$ are each independently of one another hydrogen or $C_1$–$C_{10}$alkyl; $R_5 \neq R_6 \neq R_7$;

L is a straight-chain or branched alkylene group which may be interrupted by 1 to 5 oxygen atoms or by a —C(O)—O— group which may be substituted by $C_1$–$C_{10}$alkoxy or $C_1$–$C_{10}$-alkylcarbonyloxy; and X is $$-\overset{O}{\underset{\|}{C}}-O-,$$

the carbonyl carbon atom being bound to the nitrogen atom of the $$-\underset{R_4}{\overset{|}{N}}-$$

moiety; or —SO$_2$—.

Some of the benzotriazole derivatives of formula (1) are known compounds. Some of them are, however, novel compounds. These novel compounds correspond to formula (4)

[Chemical structure of benzotriazole derivative with HO, CH3, and carbamate-linked 2-ethylhexyl group]

or to formula (5)

[Chemical structure of benzotriazole derivative with H3C-O substituent, HO group, and carbamate-linked 2-ethylhexyl group]

The benzotriazole derivatives of formula (1) can be prepared by reacting the chromophore of formula (6a)

[Chemical structure showing benzotriazole with R1, R2, R3, R4, HO and HN groups]

with the compound of formula (6a)

[Chemical structure showing benzotriazole with R1, R2, R3, R4, HO and HN groups]

with the compound of formula (6b)

$$Cl-X-(L)_p-\underset{R_7}{\overset{R_5}{\underset{|}{\overset{|}{C^*}}}}-R_6.$$

$R_1$, $R_2$, $R_3$, $R_4$, $R_5$, $R_6$, $R_7$, X, L and p in this case have the meanings given for the compounds of formula (1).

A detailed description of the preparation may be found in U.S. Pat. No. 5,500,332.

The compound of formula (6a) may be prepared starting from o-nitroaniline, 4-chloro-2-nitroaniline and m-amino- or m-aminoalkyl-substituted phenols by generally known preparation methods which are described, inter alia, in U.S. Pat. No. 3,813,255. 2-(2'-Hydroxy-4'-aminophenyl) benzotriazole, for example, can be prepared by reacting 2-nitrobenzenediazonium chloride with 3-aminophenol and by subsequent reductive ring closure of the azo dye to the desired benzotriazole.

The benzotriazole derivatives of formula (1) are known as UV absorbers for technical applications, e.g. for plastic materials, paints systems and films, natural or synthetic resins, waxy materials or rubber. They are also, surprisingly, suitable for protecting human and animal skin and hair from the harmful effects of UV radiation and can therefore be used as light stabilisers in cosmetic, pharmaceutical and veterinary preparations. As water-soluble compounds they are usually used in dissolved form.

Accordingly, this invention also relates to a cosmetic preparation comprising at least one compound of formula (1) as well as cosmetically compatible carriers or auxiliaries.

The novel cosmetic preparation preferably comprises 0.25 to 15% by weight, based on the total weight of the composition, of a benzotriazole derivative of formula (1).

In addition to the novel UV absorbers, the cosmetic formulation for hair can also contain one or more than one further UV protective of the following substance classes:

1. p-aminobenzoic acid derivatives, typically 2-ethylhexyl 4-dimethylaminobenzoate;
2. salicylic acid derivatives, typically 2-ethylhexyl salicylate;
3. benzophenone derivatives, typically 2-hydroxy-4-methoxybenzophenone and its 5-sulfonic acid derivative;

4. dibenzoylmethane derivatives, typically 1-(4-tert-butylphenyl)-3-(4-methoxyphenyl)-propane-1,3-dione;
5. diphenylacrylates, typically 2-ethylhexyl-2-cyano-3,3-diphenylacrylate and 3-(benzofuranyl)-2-cyanoacrylate;
6. 3-imidazol-4-yl-acrylic acid and 3-imidazol-4-yl-acrylate;
7. benzofuran derivatives, preferably 2-(p-aminophenyl) benzofuran derivatives, disclosed in EP-A-582,189, U.S. Pat. No. 5,338,539, U.S. Pat. No. 5,518,713 and in EP-A-613,893;
8. polymeric UV absorbers, such as the benzylidenemalonate derivatives described, inter alia, in EPA-709,080;
9. cinnamic acid derivatives, typically the 2-ethylhexyl 4-methoxycinnamate or isoamylate or cinnamic acid derivatives disclosed, inter alia, in U.S. Pat. No. 5,601,811 and WO 97/00851;
10. camphor derivatives, typically 3-(4'-methyl) benzylidenebornan-2-one, 3-benzylidenebornan-2one, N-[2(and 4)-2-oxyborn-3-ylidenemethyl)benzyl] acrylamide polymer, 3-(4'-trimethylammonium) benzylidenebornan-2-one methyl sulfate, 3,3'-(1,4-phenylenedimethine)-bis(7,7-dimethyl-2-oxo-bicyclo-[2.2.1]heptane-1-methansulfonic acid) and the salts thereof, 3-(4'-sulfo)benzylidenebornan-2-one and the salts thereof;
11. trianilino-s-triazine derivatives, typically 2,4,6-trianiline-(p-carbo-2'-ethyl-1'-oxi)-1,3,5-triazines as well as the UV absorbers disclosed in U.S. Pat. No. 5,332,568, EP-A-517,104, EP-A-507,691, WO 93/17002 and EP-A-570,838;
12. 2-hydroxyphenylbenzotriazole derivatives;
13. 2-phenylbenzimidazole-5-sulfonic acid and the salts thereof;
14. menthyl-o-aminobenzoate;
15. $TiO_2$ (coated differently), ZnO and mica.

The cosmetic formulations can be prepared by physically mixing the UV absorber(s) with the auxiliary by conventional methods, such as by simply stirring the individual components together.

The cosmetic formulations of this invention can be formulated as water-in-oil or oil-in-water emulsion, as oil-in-alcohol lotion, as vesicular dispersion of a ionic or nonionic amphiphilic lipid, as gel, solid stick or as aerosol formulation.

As water-in-oil or oil-in-water emulsion, the cosmetically compatible auxiliary preferably comprises 5 to 50% of an oil phase, 5 to 20% of an emulsifier and 30 to 90% of water. The oil phase can contain any oil suitable for cosmetic formulations, for example one or several hydrocarbon oils, wax, natural oil, silicone oil, fatty acid ester or fatty alcohol. Preferred mono- or polyols are ethanol, isopropanol, propylene glycol, hexylene glycol, glycerol and sorbitol.

To prepare the novel cosmetic formulations it is possible to use any conventionally usable emulsifier, typically one or several ethoxylated esters of natural derivatives, such as polyethoxylated ester of hydrogenated castor oil; or a silicone oil emulsifier, such as silicone polyol; a free or ethoxylated fatty acid soap; an ethoxylated fatty alcohol; a free or ethoxylated sorbitan ester; an ethoxylated fatty acid; or an ethoxylated glyceride.

The cosmetic formulations may also contain other components, such as emollients, emulsion stabilisers, skin moisturisers, suntan promoters, thickeners, such as xanthan, moisture retention agents, such as glycerol, preservatives, fragrances and colourants.

The novel cosmetic formulations are distinguished by excellently protecting human skin against the harmful effects of sunlight over a prolonged period of irradiation.

The UV absorbers of formula (1) used according to this invention are particularly suitable for protecting human hair from the harmful effects of UV radiation.

The UV absorbers are distinguished by having high substantivity for human hair, and guaranteeing high UV protection for hair.

It is possible to use, for example, the following cosmetic formulations for hair:

$a_1$) spontaneously emulsifying stock formulations, consisting of the UV absorber, PEG-6 $C_{10}$oxoalcohol and sorbitan esquioleate, which is charged with water and any quaternary ammonium compound, such as 4% minkamidopropyldimethyl-2-hydroxyethyl ammonium chloride or Quaternium 80;

$a_2$) spontaneously emulsifying stock formulation, consisting of the UV absorber, tributyl citrate and PEG-20 sorbitan monooleate, which is charged with water and any quaternary ammonium compound, such as 4% minkamidopropyldimethyl-2-hydroxyethyl ammonium chloride or Quaternium 80;

b) quat-doped solutions of the UV absorber in butyl triglycol and tributyl citrate;

c) dispersions of micronised UV absorbers obtained by known methods (precipitation from solutions or mixtures of solutions, grinding), having an average diameter of 0.05–1.0 µm in APG (e.g. Plantaren), and a quat (e.g. minkamidopropyidimethyl-2-hydroxyethyl ammonium chloride) in an aqueous formulation;

d) mixtures or solutions of the UV absorber with n-alkylpyrrolidone.

This invention also relates to a method of treating human hair to protect it from the harmful effects of UV radiation. This method comprises treating hair with a shampoo, lotion or gel, or with an emulsion for rinsing, before or after shampooing, before or after dyeing or removing dye, before or after a perming or straightening process; with a lotion, foam or gel for setting; with a lotion, foam or gel for brushing or waving; with a hair lacquer; with a composition for perming or straightening hair, for dyeing or removing dye, which shampoo, lotion, gel, emulsion, foam, hair lacquer or composition for perming, straightening, dyeing or removing dye comprises at least one benzotriazole compound of formula (1).

The following non-limitative Examples illustrate the invention in more detail.

PREPARATION OF NOVEL COMPOUNDS

EXAMPLE 1

3.3 g of o-nitroaniline are diazotised and the diazonium compound so obtained is coupled to a solution of 4.1 g of 3-amino-o-cresol in 60 ml of water and 3.3 g of concentrated hydrochloric acid. In the course of the coupling reaction, the coupling suspension is diluted with 250 ml of water to improve the stirrability and is then stirred for 3 hours at 25° C., and the red suspension is collected by suction filtration. To purify the water-moist product it is stirred in 250 ml of ethanol at 25° C. for 1 hour and then filtered. The red azo dye of formula

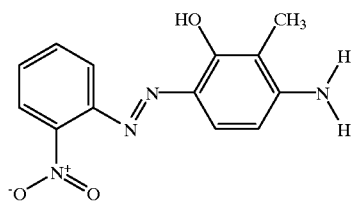

(101a)

so obtained is made into a slurry in 100 ml of water and 28.8 ml of 10 N sodium hydroxide solution at 25° C. Subsequently, 6 g of zinc dust are added and the mixture is stirred for 16 hours at 25° C. This mixture is then heated to 40° C. and another 2 g of zinc dust and 2 ml of 10 N sodium hydroxide solution are added. After stirring for 4 hours at 35–40° C., the yellow-green suspension is clarified by filtration using a filter auxiliary and neutralised from pH 13.8 to pH 6.6 with 16 ml of concentrated hydrochloric acid. A beige product precipitates which, after stirring for 1 hour at 25° C., is isolated by filtration. After recrystallising three times from isopropyl alcohol, 1200 mg of a pure product of formula

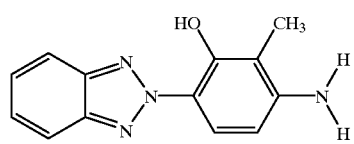

(101b)

are obtained having a melting point of 236–236.5° C.

1000 mg of this compound are made into a slurry in 30 ml of ethyl acetate and are then charged with 2 ml of water and 0.53 g of potassium hydrogencarbonate and cooled to 10° C.

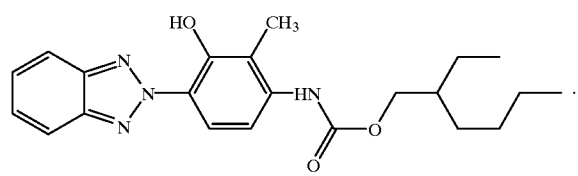

(101)

The melting point is 124–125° C.

$\epsilon$=24139 I/(mol/cm) (in ethanol); $\lambda_{max}$=340 nm.

EXAMPLE 2

67 g of 4-methoxy-2-nitroaniline are diazotised in water in conventional manner and the diazonium compound so obtained is then coupled to 64.4 g of 3-aminophenol at pH 3. The red azo dye of formula

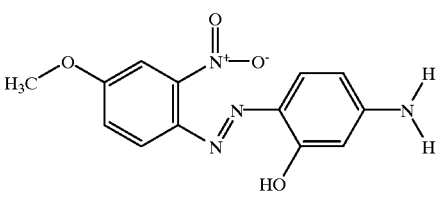

(102a)

is isolated and processed in a water-moist state.

The above azo dye is made into a slurry in 1000 ml of water and 140 ml of 10N sodium hydroxide solution at 25° C., to which 90 g of zinc dust are then added in portions (over 1 hour), the temperature rising to 36° C. After stirring for 15 hours, the temperature drops to 25° C. The mixture is heated to 40° C. and another 55 g of zinc dust and 100 ml of 10 N sodium hydroxide are then added in portions. The reaction is followed by thin-layer chromatography and is complete after 3 hours and at 40° C. The reaction mixture is clarified by filtration and the filtrate is adjusted to pH 6.4 with 250 ml of concentrated hydrochloric acid and the precipitated product is filtered after 1 hour at 25° C. After two recrystallisations, 5.7 g of the pure product of formula

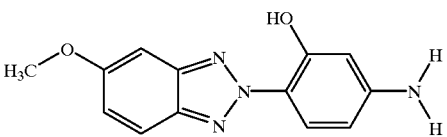

(102b)

are obtained.

Melting point: 190–191° C.

3.84 g of this compound are stirred into 100 ml of ethyl acetate and are then charged with 8 ml of water and 1.92 g of potassium hydrogencarbonate and cooled to 10° C. 3 g of 2-ethylhexyl chloroformate are then added dropwise over 45 minutes. The temperature is allowed to rise to 25° C. After stirring for 4 hours, the phases are separated in a separating funnel and the acetate phase is extracted with a mixture of 120 ml of water, 16 ml of 2N sulfuric acid and 60 ml of 10% brine. After separation, the product is clarified by filtration with activated carbon, dried with sodium sulfate and concentrated at reduced pressure. The solidified residue is pounded together with 200 ml of water and filtered. Recrystallisation from 100 ml of ethanol affords 3.3 g of the enantiomer mixture of formula

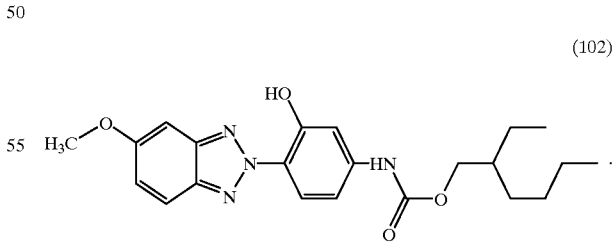

(102)

Melting point: 122–124° C.

$\epsilon$=32152I(mol/cm) in ethanol; $\lambda_{max}$=353 nm.

APPLICATION EXAMPLES

EXAMPLE 3

Composition of a cosmetic formulation with the benzotriazole compound of formula (101) from Example 1 (the individual components are named according to CTFA or INCI):

| | | |
|---|---|---|
| ($a_1$) ceteareth 6 (and) stearyl alcohol | 2.0% |
| ($a_2$) ceteareth 25 | 2.0% |
| ($a_3$) cetearyl alcohol | 5.0% |
| ($a_4$) caprylic/capric triglyceride | 5.0% |
| ($a_5$) cetearyl octanate | 10.0% |
| ($a_6$) Vaseline | 5.0% |
| ($a_7$) compound of formula (101) | 4.0% |
| ($b_1$) propylene glycol | 3.0% |
| ($b_2$) carbopol 934 | 0.2% |
| ($b_3$) $H_2O$ | 63.53% |
| (c) triethanol amine | 0.27% |

Components ($a_1$)–($a_7$) (=phase A) and ($b_1$)–($b_3$) (=phase B) are heated to 75–80° C. Phase B is then added to phase A and homogenised. Component (c) (=phase C) is then added and again homogenised.

This O/W emulsion has a sunscreen factor of 4.

The UVA/UVB ratio is 1.23, which is a very good value for a cosmetic sunscreen formulation.

The sunscreen factors are determined according to the method of Diffey and Robson, J. Soc. Cosmet. Chem. 40, 127–133 (1989) using an SPF (sunproof factor) analyser (Optometrix, SPF 290).

EXAMPLE 4

Composition of a cosmetic formulation with the benzotriazole compound of formula (102) from Example 2 (the individual components are named according to CTFA or INCI):

| | | |
|---|---|---|
| ($a_1$) dimethicone | 2.0% |
| ($a_2$) isopropyl myristate | 9.0% |
| ($a_3$) stearyl alcohol | 10.0% |
| ($a_4$) stearic acid | 4.0% |
| ($a_5$) octyl methoxycinnamate | 4.0% |
| ($b_1$) triethanolamine | 1.2% |
| ($b_2$) carbomer 934 (1%) | 5.0% |
| ($b_3$) $H_2O$ | 64.8% |

Components ($a_1$–$a_5$) (=phase A) are homogenised separately and very carefully and are then, like components ($b_1$)–($b_3$) (=phase B), heated separately to 75–80° C. Phase B is then added to phase A with vigorous stirring. With stirring, the mixture is allowed to cool.

The sunscreen factor of this suntan cream is 6 (determined using the SPF analyser SPF 290 of Optometrix).

EXAMPLES 5 TO 33

Compositions of cosmetic formulations with the benzotriazole compounds given in Table 1. The remaining components and the preparation process correspond to Example 1.

TABLE 1

| Ex. No. | $R_1$ | $R_2$ | $R_3$ | $R_4$ | L | $R_5$ | $R_6$ | $R_7$ |
|---|---|---|---|---|---|---|---|---|
| 5 | H | 5-F | H | H | $CH_2$ | H | $C_2H_5$ | $C_4H_9$ |
| 6 | H | 5-Cl | H | H | $CH_2$ | H | $C_2H_5$ | $C_4H_9$ |
| 7 | H | 5-F | H | H | $CH_2$ | H | $C_2H_5$ | $C_4H_9$ |
| 8 | H | H | H | $CH_2$—$COOCH_3$ | $CH_2$ | H | $C_2H_5$ | $C_4H_9$ |
| 9 | H | H | H | $CH_2$—$COOCH_3$ | $CH_2$ | H | $C_2H_5$ | $C_4H_9$ |
| 10 | H | H | H | $CF_2CF_3$ | $CH_2$ | $CH_3$ | $C_2H_5$ | $C_4H_9$ |
| 11 | H | H | H | H | $(CH_2)_2$ | H | $C_2H_5$ | $C_4H_9$ |
| 12 | H | H | 6'-OH | H | $CH_2$ | H | $C_2H_5$ | $C_4H_9$ |
| 13 | H | H | 6'-OH | $C_2H_5$ | $CH_2$ | H | $C_2H_5$ | $C_4H_9$ |
| 14 | H | H | 6'-OH | $CH_3$ | $CH_2$ | H | $C_2H_5$ | $C_4H_9$ |
| 15 | 6-$CH_3O$ | 5-$CH_3O$ | H | $C_2H_5$ | $CH_2$ | H | $C_2H_5$ | $C_4H_9$ |
| 16 | H | 5-$CH_3O$ | H | $C_2H_5$ | $CH_2$ | H | $C_2H_5$ | $C_4H_9$ |
| 17 | H | 5-Cl | H | sec-butyl | $CH_2$ | H | $C_2H_5$ | $C_4H_9$ |
| 18 | H | 5-sec-$C_4H_9O$ | H | sec-butyl | $CH_2$ | H | $C_2H_5$ | $C_4H_9$ |
| 19 | H | 5-$CH_3O$ | H | sec-butyl | $CH_2$ | H | $C_2H_5$ | $C_4H_9$ |
| 20 | H | H | 5'-Cl | sec-butyl | $CH_2$ | H | $C_2H_5$ | $C_2H_5$ |
| 21 | H | H | 5'-Cl | sec-butyl | $CH_2$ | H | $CH_3$ | $C_2H_5$ |
| 22 | H | H | 5'-F | sec-butyl | $CH_2$ | H | $CH_3$ | $C_4H_9$ |
| 23 | 6-F | 5-F | H | $CH_2SO_2$-o-s-$C_4H_9$ | $CH_2$ | H | $C_2H_5$ | $C_4H_9$ |
| 24 | H | 5-s-$C_4H_9$-S | H | sec-butyl | $CH_2$ | H | $C_2H_5$ | $C_4H_9$ |
| 25 | H | 5-s-$(C_4H_9)N$ | H | ethyl | $CH_2$ | H | $C_2H_5$ | $C_4H_9$ |
| 26 | H | H | H | H | $CH_2OCH_2CH_2O$ | H | $C_2H_5$ | $C_4H_9$ |
| 27 | H | H | H | H | $(CH_2OCH_2CH_2O)_2$ | H | $C_2H_5$ | $C_4H_9$ |
| 28 | H | H | H | H | $CH_2COOCH_2$ | H | $C_2H_5$ | $C_4H_9$ |
| 29 | H | H | H | H | $CH_2\overset{O}{\overset{\|}{C}}$—$OCH_2$ | H | $C_2H_5$ | $C_4H_9$ |
| 30 | H | H | H | H | $CH_2COOCH_2CH(OCOCH_3)CH_2O$ | H | $C_2H_5$ | $C_4H_9$ |

TABLE 1-continued

| Ex. No. | $R_1$ | $R_2$ | $R_3$ | $R_4$ | L | $R_5$ | $R_6$ | $R_7$ |
|---|---|---|---|---|---|---|---|---|
| 31 | H | H | H | H | 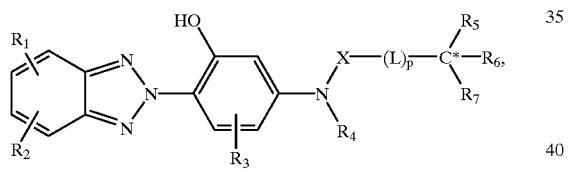 | H | $C_2H_5$ | $C_4H_9$ |
| 32 | H | H | H | H | 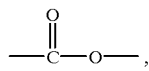 | H | $C_2H_5$ | $C_4H_9$ |
| 33 | H | H | H | H |  |  H | $C_2H_5$ | $C_4H_9$ |

What is claimed is:

1. A method of protecting human and animal hair and skin from the harmful effects of UV radiation, which comprises contacting the hair and skin with an effective amount of a benzotriazole derivative of the formula $$\text{(1)}$$

wherein $R_1$, $R_2$ and $R_3$ are each independently of one another hydrogen; straight-chain or branched $C_1$–$C_{22}$alkyl; hydroxy; carboxy; carbo-$C_1$–$C_{22}$alkoxy; nitro; $C_2$–$C_{22}$alkylcarbonylamino; $C_5$–$C_8$cycloalkyl; carbamoyl; sulfonyl; sulfamoyl; sulfonamido; $C_2$–$C_{22}$alkylcarbonyloxy; cyano; halogen; $C_6$–$C_{12}$aryl or $C_4$–$C_{12}$heteroaryl which are unsubstituted or substituted by one or several $C_1$–$C_4$alkyl; $C_7$–$C_{10}$aralkyl which is unsubstituted or substituted by one or several $C_1$–$C_4$alkyl; $C_6$–$C_{12}$aryloxy; or a radical of formula $$\text{-(alkylene-Q)}_{m_1}\text{A}_1, \quad \text{(1a)}$$

wherein $A_1$ is straight-chain or branched $C_1$–$C_8$alkyl; $C_5$–$C_8$cycloalkyl; $C_6$–$C_{12}$aryl which is unsubstituted or substituted by one or several $C_1$–$C_4$alkyl; or $C_7$–$C_{10}$aralkyl which is unsubstituted or substituted by one or several $C_1$–$C_4$alkyl;

$m_1$ is 1 to 10;

Q is —O—; —S—; or —NH—; or $R_1$ and $R_2$, together with the benzene ring of the benzotriazole, are a $C_5$–$C_{18}$aryl ring or a $C_4$–$C_{16}$-heteroaryl ring, which rings are unsubstituted or substituted by $C_1$–$C_{22}$alkyl or $C_1$–$C_{22}$alkoxy;

$R_4$ is hydrogen; $C_1$–$C_{22}$alkyl which is unsubstituted or substituted by 1 to 5 halogen atoms and/or which is interrupted by a —C(O)—O— or —SO$_2$—O— group;

$R_5$, $R_6$, $R_7$ are each independently of one another hydrogen; halogen; cyano; straight-chain or branched $C_1$–$C_{22}$alkyl; straight-chain or branched $C_1$–$C_{22}$alkoxy; $C_6$–$C_{12}$aryl; straight-chain or branched $C_1$–$C_{22}$thioalkyl; mono- or di-$C_1$–$C_{22}$alkylamino; mono- or di-$C_6$–$C_{12}$-arylamino; $R_5 \neq R_6 \neq R_7$;

X is $$-\overset{\overset{\displaystyle O}{\|}}{C}-O-,$$

the carbonyl carbon atom being bound to the nitrogen atom of the $$-\overset{|}{\underset{R_4}{N}}-$$

moiety; or —SO$_2$—;

L is a divalent radical consisting of 1 to 20 atoms; and p is 0 or 1.

2. A method according to claim 1, wherein the compound of formula (1) is a 60:40 to 40:60 mixture of two enantiomers relative to the asymmetrical C* atom.

3. A method according to claim 1, which comprises using benzotriazole derivatives of formula (1), wherein L consists of 1 to 20 atoms and is a straight-chain or branched alkylene group which may be interrupted by 1 to 5 oxygen, sulfur or nitrogen atoms or by a —C(O)—O— group which is unsubstituted or substituted by $C_1$–$C_{10}$alkoxy, $C_1$–$C_{10}$alkylcarbonyloxy, $C_1$–$C_{10}$alkyl sulfide, amino, mono-$C_1$–$C_{10}$alkylamino, di-$C_1$–$C_{10}$alkylmino or halogen; or the divalent radical of a 4- to 6-membered alicyclic ring or of a heterocyclic ring containing 1 to 3 hetero atoms.

4. A method according to claim 1, which comprises using benzotriazole derivatives of formula (1), wherein L is a methine group which is unsubstituted or substituted by $C_1$–$C_{12}$alkyl or $C_1$–$C_{12}$-alkoxy, amino, mono- or di-$C_1$–$C_6$alkylamino or halogen, wherein $C_1$–$C_{12}$alkyl or $C_1$–$C_{12}$-alkoxy may be interrupted by 1 or 2 oxygen atoms.

5. A method according to claim 1, wherein, in formula (1), $R_5$, $R_6$, $R_7$ are each independently of one another hydrogen; or straight-chain or branched $C_1$–$C_{22}$alkyl.

6. A method according to claim 1, which comprises using benzotriazoles of formula

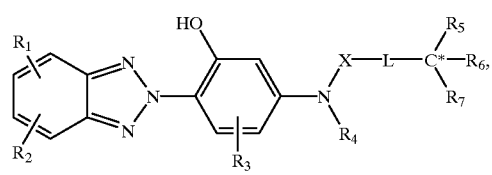

(2)

wherein $R_1$ and $R_2$ are each independently of one another hydrogen; halogen; $C_1$–$C_5$alkyl; $C_1$–$C_5$-alkoxy; mono- or di-$C_1$–$C_5$alkylamino; or $C_1$–$C_5$alkyl sulfide;

$R_3$ is hydrogen; hydroxy; or halogen;

$R_4$ is hydrogen; $C_1$–$C_5$alkyl which is unsubstituted or substituted by 1 to 5 halogen atoms and/or which may be interrupted by a —C(O)—O— or —SO$_2$—O— group;

L is a straight-chain or branched alkylene group which may be interrupted by 1 to 5 oxygen atoms or by a —C(O)—O— group which may be substituted by $C_1$–$C_{10}$alkoxy or $C_1$–$C_{10}$-alkylcarbonyloxy; and $R_5$, $R_6$, $R_7$ are each independently of one another hydrogen or $C_1$–$C_{10}$alkyl; $R_5 \neq R_6 \neq R_7$; and X is

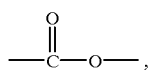, the carbonyl carbon atom being bound to the nitrogen atom of the

moiety; or —SO$_2$—.

7. A method according to claim 6, which comprises using benzotriazoles of formula

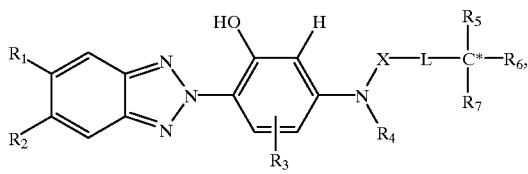

(3)

wherein $R_1$ and $R_2$ are each independently of the other hydrogen; halogen; $C_1$–$C_5$alkyl; $C_1$–$C_5$alkoxy; or $C_1$–$C_5$alkyl sulfide;

$R_3$ is hydrogen; halogen or hydroxy;

$R_4$ is hydrogen; $C_1$–$C_5$alkyl which is unsubstituted or substituted by 1 to 5 halogen atoms and/or which may be interrupted by a —C(O)—O— or —SO$_2$—O— group;

$R_5$, $R_6$, $R_7$ are each independently of one another hydrogen or $C_1$–$C_{10}$alkyl; $R_5 \neq R_6 \neq R_7$;

L is a straight-chain or branched alkylene group which may be interrupted by 1 to 5 oxygen atoms or by a —C(O)—O— group which may be substituted by $C_1$–$C_{10}$alkoxy or $C_1$–$C_{10}$-alkylcarbonyloxy; and X is

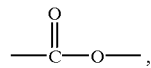

the carbonyl carbon atom being bound to the nitrogen atom of the

moiety; or —SO$_2$—.

8. A cosmetic preparation, comprising at least one benzotriazole derivative of formula (1) according to claim 1 as well as cosmetically compatible carriers or auxiliaries.

9. A cosmetic preparation according to claim 8, which comprises 0.25 to 15% by weight, based on the total weight of the composition, of a benzotriazole derivative of formula (1).

10. A process for treating human hair to protect it from the harmful effects of UV radiation, which comprises treating the hair with a shampoo, lotion, gel or emulsion for rinsing, before or after shampooing, before or after dyeing or removing the dye, before or after a perming or straightening process, with a lotion, foam or gel for setting, with a lotion, foam or gel for brushing or waving, with a hair lacquer, with a composition for perming or straightening hair, for dyeing or removing dye, which shampoo, lotion, gel, emulsion, foam, hair lacquer or composition for perming, straightening, dyeing or removing dye comprises a benzotriazole derivative of formula (1) according to claim 1.

11. A compound of formula
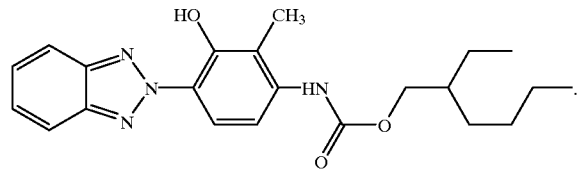
(4)
12. A compound of formula
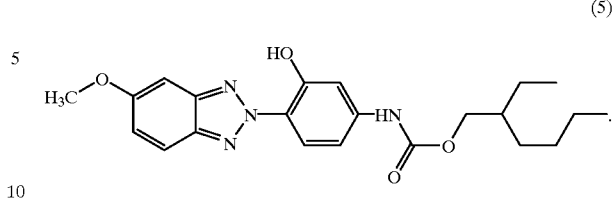
(5)
* * * * *